(12) United States Patent
Belly

(10) Patent No.: US 12,286,600 B2
(45) Date of Patent: Apr. 29, 2025

(54) FUELS

(71) Applicant: Innospec Fuel Specialties LLC, Englewood, CO (US)

(72) Inventor: Alexander John Belly, Wilmington, DE (US)

(73) Assignee: Innospec Fuel Specialties LLC, Englewood, CO (US)

( * ) Notice: Subject to any disclaimer, the term of this patent is extended or adjusted under 35 U.S.C. 154(b) by 0 days.

(21) Appl. No.: 18/223,870

(22) Filed: Jul. 19, 2023

(65) Prior Publication Data

US 2024/0043763 A1  Feb. 8, 2024

Related U.S. Application Data

(60) Provisional application No. 63/392,153, filed on Jul. 26, 2022.

(30) Foreign Application Priority Data

Aug. 23, 2022 (GB) .................................... 2212275

(51) Int. Cl.
| | |
|---|---|
| *C10L 10/16* | (2006.01) |
| *C07C 221/00* | (2006.01) |
| *C08F 8/32* | (2006.01) |
| *C10L 1/222* | (2006.01) |
| *C10L 1/236* | (2006.01) |

(52) U.S. Cl.
CPC ............ *C10L 10/16* (2013.01); *C07C 221/00* (2013.01); *C08F 8/32* (2013.01); *C10L 1/2222* (2013.01); *C10L 1/236* (2013.01); *C10L 2200/0476* (2013.01)

(58) Field of Classification Search
CPC . C07C 221/00; C08F 8/32; C10L 1/22; C10L 1/2222; C10L 1/2235; C10L 1/224; C10L 1/232; C10L 1/236; C10L 10/14; C10L 10/16; C10L 2200/0469; C10L 2200/0476; C10L 2270/026; Y02E 50/10
See application file for complete search history.

(56) References Cited

U.S. PATENT DOCUMENTS

| | | |
|---|---|---|
| 5,925,151 A | 7/1999 | DeCanio et al. |
| 7,291,758 B2 | 11/2007 | Bohnenpoll et al. |
| 9,255,236 B2 | 2/2016 | Grabarse et al. |
| 2008/0052985 A1 | 3/2008 | Stevenson et al. |
| 2008/0113890 A1 | 5/2008 | Moreton et al. |
| 2008/0307698 A1 | 12/2008 | Barton et al. |
| 2011/0258917 A1 | 10/2011 | Garcia Castro et al. |
| 2011/0315107 A1 | 12/2011 | Grabarse et al. |
| 2012/0010112 A1 | 1/2012 | Grabarse et al. |
| 2013/0031827 A1 | 2/2013 | Reid et al. |
| 2018/0237710 A1 | 8/2018 | Freer et al. |
| 2019/0218466 A1 | 7/2019 | Slade et al. |
| 2020/0024536 A1 | 1/2020 | Shanahan et al. |
| 2020/0024538 A1 | 1/2020 | Deckman et al. |
| 2020/0222855 A1* | 7/2020 | Bloom ................... C07C 67/48 |
| 2021/0277320 A1* | 9/2021 | Meyer .................. C10L 1/1973 |

FOREIGN PATENT DOCUMENTS

| | | |
|---|---|---|
| EP | 0565285 A1 | 10/1993 |
| EP | 1254889 A1 | 11/2002 |
| EP | 2631283 A1 | 8/2013 |
| EP | 4166633 A1 | 4/2023 |
| GB | 1068226 A | 5/1967 |
| GB | 2520795 A | 6/2015 |
| GB | 2546350 A | 7/2017 |
| GB | 2591005 A | 7/2021 |
| GB | 2591554 A | 8/2021 |
| GB | 2620491 A | 1/2024 |
| PL | 229728 B1 | 8/2018 |
| WO | 2006135881 A2 | 12/2006 |
| WO | 2007015080 A1 | 2/2007 |
| WO | 2009040582 A1 | 4/2009 |
| WO | 2009040583 A1 | 4/2009 |
| WO | 2010089594 A1 | 8/2010 |
| WO | 2011095819 A1 | 8/2011 |
| WO | 2013017886 A1 | 2/2013 |
| WO | 2013017887 A1 | 2/2013 |
| WO | 2013017889 A1 | 2/2013 |
| WO | 2015011506 A1 | 1/2015 |
| WO | 2015011507 A1 | 1/2015 |
| WO | 2016016641 A1 | 2/2016 |
| WO | 2017017454 A1 | 2/2017 |
| WO | 2021/126342 A1 | 6/2021 |
| WO | 2023/057748 A1 | 4/2023 |
| WO | 2023233152 A1 | 12/2023 |
| WO | 2024006694 A1 | 1/2024 |

OTHER PUBLICATIONS

GB Search Report issued for GB2212275.8 dated Nov. 24, 2022 (2 pages).
Neste: "Neste Renewable Diesel Handbook", Apr. 23, 2002, XP 093071405.
International Search Report (ISR) for PCT/GB2023/051893 mailed Sep. 21, 2023 (5 pages).
Written Opinion (WO) PCT/GB2023/051893 mailed Sep. 21, 2023 (8 pages).

* cited by examiner

*Primary Examiner* — Ellen M McAvoy
*Assistant Examiner* — Chantel Graham
(74) *Attorney, Agent, or Firm* — Shumaker, Loop & Kendrick, LLP

(57) ABSTRACT

At least one nitrogen-containing detergent to reduce the filter blocking tendency of a fuel composition having a tendency to block filters. The fuel composition includes a renewable diesel component and a biodiesel component.

22 Claims, No Drawings

FUELS

TECHNICAL FIELD AND BACKGROUND

The present invention relates to improvements in fuel compositions, and in particular to improving the properties of blended fuel compositions comprising renewable diesel and biodiesel.

Due to environmental considerations significant efforts have been made in developing alternative hydrocarbon fuels to fossil fuels to power internal combustion engines. The present invention relates in particular to alternatives to mineral diesel fuel.

One alternative fuel suitable for use in diesel engines is biodiesel. Biodiesel is produced by the transesterification of lipids obtained from plants or animals, for example tallow oil, soybean oil or other vegetable oil. Transesterification of the triglycerides obtained from these plant or animal sources with an alcohol such as methanol, ethanol or propanol produces a mono alkyl ester as the biodiesel fuel.

Renewable diesel is produced from biomass sources through biological, thermal and chemical processes. Typically renewable diesels are obtained by hydrotreatment of vegetable oils with hydrogen at elevated temperatures and pressures in the presence of a catalyst. Renewable diesel is sometimes referred to as hydrogenated vegetable oil.

Renewable diesel contains mainly saturated, straight chain or branched, aliphatic hydrocarbons. Biodiesel consists primarily of mono alkyl esters. Mineral diesel often contains aromatic and sulfated species as well as aliphatic hydrocarbons.

Due to the different chemical components of the fuels, new challenges can arise when mineral diesel is replaced partially or fully with renewable diesel and/or biodiesel.

The present invention attempts to solve some problems that may occur when blends of renewable diesel and biodiesel are used. Due to the different chemical nature of the renewable and biodiesel components of a blended fuel, problems can occur when storing the fuel, particularly if storage is at low temperatures.

Three measurements are commonly taken to assess the low temperature performance of diesel fuel. Standardised tests have been devised to measure the temperature at which the fuel hazes (the cloud point—CP), the lowest temperature at which a fuel can flow (the pour point—PP) and the lowest temperature at which fuel flows through a filter, the cold filter plugging point—CFPP); and the changes thereto caused by additives (ΔCP, ΔPP, ΔCFPP).

SUMMARY

The present invention is not about the use of nitrogen-containing detergents (as additives) to change the cloud point, pour point or cold filter plugging point of a fuel. Rather the present invention seeks to address problems that can occur in a fuel when it is above the cloud point.

Diesel vehicle fuel systems are fitted with a filter to prevent particulate matter reaching the final injection system. If such particulates are not removed, failure of the fuel injection system could result.

Problems can arise when the filter becomes blocked as this affects the rate at which fuel is delivered to the engine. This issue is different to the problems which occur during cold filter plugging where wax forms under very low temperatures and blocks the filter until the wax re-dissolves. Filter blocking can occur due to the formation of particulates within the fuel, particularly during storage. In recent years the problems with filter blocking have become more prominent. This is because in an effort to reduce emissions and improve engine performance, more sophisticated injection systems have been developed. Since these fuel injection systems operate at high temperature and pressures they are more susceptible to wear and damage if exposed to particulates in the fuel. Fuel filter pore sizes have therefore decreased and in some cases may be as low as 2 to 5 microns in diameter. The reduction in pore size of the filter has inevitably led to increased issues with filter blocking. A blocked filter will restrict or prevent fuel from reaching an engine. This can cause problems with starting the engine and a loss of power. In some instances a blocked filter can cause an engine to shut down altogether until the filter has been replaced, in order to protect the injection system, causing huge inconvenience to the user.

The present invention seeks to reduce the filter blocking tendency of fuels containing a blend of renewable diesel and biodiesel fuels. These fuels are different in nature to mineral diesel fuels and blends containing mineral diesel.

DETAILED DESCRIPTION

According to a first aspect of the present invention there is provided the use of at least one nitrogen-containing detergent to reduce the filter blocking tendency of a fuel composition having a tendency to block filters, wherein the fuel composition comprises a renewable diesel component and a biodiesel component.

According to a second aspect of the present invention there is provided a method of reducing the filter blocking tendency of a fuel composition having a tendency to block filters and which comprises a biodiesel component and a renewable diesel component, the method comprising dosing into the fuel at least one nitrogen-containing detergent.

According to a third aspect of the present invention there is provided a fuel composition comprising a renewable diesel component, a biodiesel component and at least one nitrogen-containing detergent: wherein the fuel composition has a reduced filter blocking tendency compared with an otherwise identical fuel composition which does not comprise the nitrogen-containing detergent and has a tendency to block filters.

Preferred features of the first, second and third aspects of the invention will now be described.

The first, second and third aspects of the present invention relate to at least one nitrogen-containing detergent. This can involve one nitrogen-containing detergent or a mixture of two or more nitrogen-containing detergents. References herein to the nitrogen-containing detergent include embodiments in which two or more nitrogen-containing detergents are present.

The present invention relates to reducing the filter blocking tendency of fuel compositions comprising a biodiesel component and a renewable diesel component.

The fuel compositions may optionally further comprise a mineral diesel component. In preferred embodiments the fuel compositions do not comprise a mineral diesel component.

In this specification by biodiesel we mean to refer to esters of fatty acids. Such fuels are commonly referred to as first generation biodiesel. Biodiesel as defined herein contains esters of, for example, vegetable oils, animal fats and used cooking fats. This form of biodiesel may be obtained by transesterification of oils, with an alcohol, usually a mono-alcohol, usually in the presence of a catalyst. The fatty acids used to produce the fuel may originate from a wide variety of natural sources including, but not limited to, vegetable oil, canola oil, safflower oil, sunflower oil, nasturtium seed oil, mustard seed oil, olive oil, sesame oil, soybean oil, corn oil, peanut oil, cottonseed oil, rice bran oil, babassu nut oil, castor oil, palm oil, rapeseed oil, low erucic acid rapeseed oil, palm kernel oil, lupin oil, jatropha oil, coconut oil, flaxseed oil, evening primrose oil, jojoba oil, camelina oil, tallow, beef tallow, butter, chicken fat, lard, dairy butterfat, shea butter, used frying oil, oil miscella, used cooking oil, yellow trap grease, hydrogenated oils, derivatives of the oils, fractions of the oils, conjugated derivatives of the oils, and mixtures of any thereof.

In this specification by renewable diesel we mean to refer to diesel fuel obtained by the hydrodeoxygenation of fats and oils. Such fuels are often referred to as second generation biodiesel and are derived from renewable resources such as vegetable oils and animal fats and processed, often in the refinery, using, for example, hydroprocessing such as the H-Bio process developed by Petrobras. Second generation biodiesel is marketed by ConocoPhillips as Renewable Diesel and by Neste as NExBTL Renewable diesel fuels are sometimes known as hydrogenated vegetable oils (or HVOs).

The fuel composition comprises a renewable diesel component and a biodiesel component. Preferably the renewable diesel component makes up at least 10 vol % of all fuel components present in the composition, preferably at least 30 vol %, more preferably at least 40 vol %, preferably at least 50 vol %.

Suitably the renewable diesel component makes up at least 60 vol %, suitably at least 70 vol %, for example, at least 75 vol % of all fuel components in the fuel composition.

The renewable diesel component may provide up to 99 vol % of all fuel components present in the fuel composition, preferably up to 95 vol %, suitably up to 90 vol %, for example up to 85 vol %.

The biodiesel component may make up at least 1 vol % of all fuel components present in the fuel composition, preferably at least 3 vol %, suitably at least 5 vol %, preferably at least 8 vol %, for example at least 10 vol %. The biodiesel component may make up at least 12 vol % of all fuel components present in the fuel composition, for example at least 15 vol %.

The biodiesel component may provide up to 90 vol % of all fuel components present in the fuel composition, for example up to 70 vol %, suitably up to 50 vol %, for example up to 40 vol % or up to 30 vol %. The biodiesel component may provide up to 25 vol % of all fuel components present in the fuel composition.

In some preferred embodiments, the fuel composition comprises from 1 to 40 vol %, preferably 5 to 35 vol % of a biodiesel component and from 60 to 99 vol %, preferably 65 to 95 vol % of a renewable diesel component.

In some further preferred embodiments, the fuel composition comprises from 10 to 30 vol %, preferably 15 to 25 vol % of a biodiesel component and from 70 to 90 vol %, preferably from 75 to 85 vol % of a renewable diesel component.

In some especially preferred embodiments, the fuel composition comprises approximately 80 vol % of a renewable diesel component and approximately 20 vol % of a biodiesel component.

Preferably the fuel composition comprises less than 10 vol % mineral diesel, preferably less than 5 vol %, more preferably less than 3 vol %, preferably less than 1 vol %, for example less than 0.5 vol % or less than 0.1 vol % mineral diesel.

In some embodiments the fuel composition may comprise trace amounts of mineral diesel. Such trace amounts may be present due to contamination of the fuel composition during transport and/or storage using pipelines and/or tanks that previously contained mineral diesel.

In especially preferred embodiments, the fuel composition does not comprise a mineral diesel component.

In the present invention the filter blocking tendency of the fuel compositions comprising a biodiesel component and a renewable diesel component is reduced by the addition of at least one nitrogen-containing detergent.

The present invention involves the use of at least one nitrogen-containing detergent as an additive. Thus the invention may include the use of one nitrogen-containing detergent as an additive or the use of multiple nitrogen-containing detergents as multiple additives.

For the avoidance of doubt each nitrogen-containing detergent used (i.e. as an additive) in the present invention may comprise a mixture of compounds and references to a nitrogen-containing detergent (or to an additive) or to the nitrogen-containing detergent (or to the additive) include mixtures, unless otherwise stated. In particular mixtures of isomers and mixtures of homologues are within the scope of the invention. The skilled person will appreciate that commercial sources of some of the nitrogen-containing detergent compounds described herein may comprise mixtures of isomers and/or mixtures of homologues.

The invention relates to the use of at least one nitrogen-containing detergent. Preferably the at least one nitrogen-containing detergents is selected from one or more of:
  (a) a quaternary ammonium salt;
  (b) the reaction product of a carboxylic acid-derived acylating agent and an amine;
  (c) the product of a Mannich reaction between an aldehyde, an amine and an optionally substituted phenol;
  (d) the reaction product of a carboxylic acid-derived acylating agent and hydrazine;
  (e) a salt formed by the reaction of a carboxylic acid with di-n-butylamine or tri-n-butylamine; and
  (f) the reaction product of a hydrocarbyl-substituted dicarboxylic acid or anhydride and an amine compound or salt which product comprises at least one amino triazole group.

The at least one nitrogen-containing detergent is preferably selected from one or more of:
  (a) a quaternary ammonium salt;
  (b) the reaction product of a carboxylic acid-derived acylating agent and an amine; and
  (c) the product of a Mannich reaction between an aldehyde, an amine and an optionally substituted phenol.

The at least one nitrogen-containing detergent may comprise (a) a quaternary ammonium salt.

Component (a) may comprise any suitable quaternary ammonium salt.

Preferably the quaternary ammonium salt is the reaction product of a compound including a tertiary amine group and a quaternising agent.

Any suitable quaternising agent may be used. The quaternising agent may suitably be selected from esters and non-esters.

Suitable quaternising agents include esters of a carboxylic acid, dialkyl sulfates, benzyl halides, hydrocarbyl substituted carbonates, hydrocarbyl substituted epoxides optionally in combination with an acid, alkyl halides, alkyl sulfonates, sultones, hydrocarbyl substituted phosphates, hydrocarbyl substituted borates, alkyl nitrites, alkyl nitrates, hydroxides, N-oxides, chloroacetic acid or salts thereof, or mixtures thereof.

In some preferred embodiments, quaternising agents used to form the quaternary ammonium salts for use in the present invention are esters.

Preferred ester quaternising agents are compounds of formula (I):

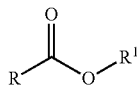

I in which R is an optionally substituted alkyl, alkenyl, aryl or alkylaryl group and $R^1$ is a C1 to C22 alkyl, aryl or alkylaryl group. The compound of formula (I) is suitably an ester of a carboxylic acid capable of reacting with a tertiary amine to form a quaternary ammonium salt.

Suitable quaternising agents include esters of carboxylic acids having a pKa of 3.5 or less.

The compound of formula (I) is preferably an ester of a carboxylic acid selected from a substituted aromatic carboxylic acid, an α-hydroxycarboxylic acid and a polycarboxylic acid.

In some preferred embodiments the compound of formula (I) is an ester of a substituted aromatic carboxylic acid and thus R is a substituted aryl group.

Preferably R is a substituted aryl group having 6 to 10 carbon atoms, preferably a phenyl or naphthyl group, most preferably a phenyl group. R is suitably substituted with one or more groups selected from carboalkoxy, nitro, cyano, hydroxy, $SR^5$ or $NR^5R^6$. Each of $R^5$ and $R^6$ may be hydrogen or optionally substituted alkyl, alkenyl, aryl or carboalkoxy groups. Preferably each of $R^5$ and $R^6$ is hydrogen or an optionally substituted C1 to C22 alkyl group, preferably hydrogen or a C1 to C16 alkyl group, preferably hydrogen or a C1 to C10 alkyl group, more preferably hydrogen or a C1 to C4 alkyl group. Preferably $R^6$ is hydrogen and $R^6$ is hydrogen or a C1 to C4 alkyl group. Most preferably $R^5$ and $R^6$ are both hydrogen. Preferably R is an aryl group substituted with one or more groups selected from hydroxyl, carboalkoxy, nitro, cyano and $NH_2$. R may be a poly-substituted aryl group, for example trihydroxyphenyl. In some embodiments R may be a hydrocarbyl substituted aryl group, for example an alkyl substituted aryl group. In some embodiments R may be an aryl group substituted with a hydroxy group and a hydrocarbyl group, such as an alkyl group, for example as described in EP2631283.

Preferably R is a mono-substituted aryl group. Preferably R is an ortho substituted aryl group. Suitably R is substituted with a group selected from OH, $NH_2$, $NO_2$ or COOMe. Preferably R is substituted with an OH or $NH_2$ group. Suitably R is a hydroxy substituted aryl group. Most preferably R is a 2-hydroxyphenyl group.

Preferably $R^1$ is an alkyl, aralkyl or alkaryl group. $R^1$ may be a C1 to C16 alkyl group, preferably a C1 to C10 alkyl group, suitably a C1 to C8 alkyl group. $R^1$ may be C7 to C16 aralkyl or alkaryl group, preferably a C7 to C10 aralkyl or alkaryl group. $R^1$ may be methyl, ethyl, propyl, butyl, pentyl, benzyl or an isomer thereof. Preferably $R^1$ is benzyl or methyl. Most preferably $R^1$ is methyl.

Especially preferred compounds of formula (I) are lower alkyl esters of salicylic acid such as methyl salicylate, ethyl salicylate, n and i propyl salicylate, and butyl salicylate, preferably methyl salicylate.

In some embodiments the compound of formula (I) is an ester of an α-hydroxycarboxylic acid. In such embodiments the compound has the structure:

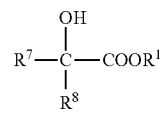

wherein $R^7$ and $R^8$ are the same or different and each is selected from hydrogen, alkyl, alkenyl, aralkyl or aryl. Compounds of this type suitable for use herein are described in EP 1254889.

Examples of compounds of formula (I) in which RCOO is the residue of an α-hydroxycarboxylic acid include methyl-, ethyl-, propyl-, butyl-, pentyl-, hexyl-, benzyl-, phenyl-, and allyl esters of 2-hydroxyisobutyric acid; methyl-, ethyl-, propyl-, butyl-, pentyl-, hexyl-, benzyl-, phenyl-, and allyl esters of 2-hydroxy-2-methylbutyric acid; methyl-, ethyl-, propyl-, butyl-, pentyl-, hexyl-, benzyl-, phenyl-, and allyl esters of 2-hydroxy-2-ethylbutyric acid; methyl-, ethyl-, propyl-, butyl-, pentyl-, hexyl-, benzyl-, phenyl-, and allyl esters of lactic acid; and methyl-, ethyl-, propyl-, butyl-, pentyl-, hexyl-, allyl-, benzyl-, and phenyl esters of glycolic acid. Of the above, a preferred compound is methyl 2-hydroxyisobutyrate.

In some embodiments the compound of formula (I) is an ester of a polycarboxylic acid. In this definition we mean to include dicarboxylic acids and carboxylic acids having more than 2 acidic moieties. In such embodiments RCOO is preferably present in the form of an ester, that is the one or more further acid groups present in the group R are in esterified form. However embodiments in which not all acid groups are esterified are within the invention. Mixed esters of polycarboxylic acids may also be used. Preferred esters are C1 to C4 alkyl esters.

The ester quaternising agent may be selected from the diester of oxalic acid, the diester of phthalic acid, the diester of maleic acid, the diester of malonic acid or the diester of citric acid. One especially preferred compound of formula (I) is dimethyl oxalate.

In preferred embodiments the compound of formula (I) is an ester of a carboxylic acid having a pKa of less than 3.5. In such embodiments in which the compound includes more than one acid group, we mean to refer to the first dissociation constant.

The ester quaternising agent may be selected from an ester of a carboxylic acid selected from one or more of oxalic acid, phthalic acid, salicylic acid, maleic acid, malonic acid, citric acid, nitrobenzoic acid, aminobenzoic acid and 2,4,6-trihydroxybenzoic acid.

Preferred ester quaternising agents include dimethyl oxalate, methyl 2-nitrobenzoate and methyl salicylate.

In some preferred embodiments, quaternising agents used to form the quaternary ammonium salts for use in the present invention are esters selected from dimethyl oxalate, methyl 2-nitrobenzoate and methyl salicylate, preferably dimethyl oxalate and methyl salicylate.

Suitable non-ester quaternising agents include dialkyl sulfates, benzyl halides, hydrocarbyl substituted carbonates, hydrocarbyl substituted epoxides optionally in combination with an acid, alkyl halides, alkyl sulfonates, sultones, hydrocarbyl substituted phosphates, hydrocarbyl substituted borates, alkyl nitrites, alkyl nitrates, hydroxides, N-oxides, chloroacetic acid or salts thereof, or mixtures thereof.

In some embodiments the quaternary ammonium salt may be prepared from, for example, an alkyl or benzyl halide (especially a chloride) and then subjected to an ion exchange reaction to provide a different anion as part of the quaternary ammonium salt. Such a method may be suitable to prepare quaternary ammonium hydroxides, alkoxides, nitrites or nitrates.

Preferred non-ester quaternising agents include dialkyl sulfates, benzyl halides, hydrocarbyl substituted carbonates, hydrocarbyl substituted epoxides in combination with an acid, alkyl halides, alkyl sulfonates, sultones, hydrocarbyl substituted phosphates, hydrocarbyl substituted borates, N-oxides, chloroacetic acid or salts thereof, or mixtures thereof.

Suitable dialkyl sulfates for use herein as quaternising agents include those including alkyl groups having 1 to 10, preferably 1 to 4 carbons atoms in the alkyl chain. A preferred compound is dimethyl sulfate.

Suitable benzyl halides include chlorides, bromides and iodides. The phenyl group may be optionally substituted, for example with one or more alkyl or alkenyl groups, especially when the chlorides are used. A preferred compound is benzyl bromide.

Suitable hydrocarbyl substituted carbonates may include two hydrocarbyl groups, which may be the same or different. Each hydrocarbyl group may contain from 1 to 50 carbon atoms, preferably from 1 to 20 carbon atoms, more preferably from 1 to 10 carbon atoms, suitably from 1 to 5 carbon atoms. Preferably the or each hydrocarbyl group is an alkyl group. Preferred compounds of this type include diethyl carbonate and dimethyl carbonate.

Suitable hydrocarbyl substituted epoxides have the formula:

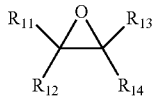

wherein each of $R^{11}$, $R^{12}$, $R^{13}$ and $R^{14}$ is independently hydrogen or a hydrocarbyl group having 1 to 50 carbon atoms. Examples of suitable epoxides include ethylene oxide, propylene oxide, butylene oxide, styrene oxide and stilbene oxide. The hydrocarbyl epoxides are used as quaternising agents in combination with an acid.

In some embodiments the compound including a tertiary amine group also includes an acid functional group. In these embodiments if an epoxide is used as the quaternising agent, a separate acid does not need to be added. However, in other embodiments an acid, for example acetic acid, may be used.

Especially preferred epoxide quaternising agents are propylene oxide and styrene oxide, optionally in combination with an additional acid.

Suitable alkyl halides for use herein include chlorides, bromides and iodides.

Suitable alkyl sulfonates include those having 1 to 20, preferably 1 to 10, more preferably 1 to 4 carbon atoms.

Suitable sultones include propane sultone and butane sultone.

Suitable hydrocarbyl substituted phosphates include monoalkyl phosphates, dialkyl phosphates, trialkyl phosphates and O,O-dialkyl dithiophosphates. Preferred alkyl groups have 1 to 12 carbon atoms.

Suitable hydrocarbyl substituted borate groups include alkyl borates having 1 to 12 carbon atoms.

Preferred alkyl nitrites and alkyl nitrates have 1 to 12 carbon atoms.

Preferably, the non-ester quaternising agent is selected from dialkyl sulfates, benzyl halides, hydrocarbyl substituted carbonates, hydrocarbyl substituted epoxides optionally in combination with an additional acid, chloroacetic acid or a salt thereof, and mixtures thereof.

Especially preferred non-ester quaternising agents for use herein are hydrocarbyl substituted epoxides in combination with an acid. These may include embodiments in which a separate acid is provided or embodiments in which the tertiary amine compound that is being quaternised additionally includes an acid group. Preferably, the tertiary amine compound that is being quaternised additionally includes an acid group.

Preferred quaternising agents for use herein include dimethyl oxalate, methyl 2-nitrobenzoate, methyl salicylate, chloroacetic acid or a salt thereof, and styrene oxide or propylene oxide optionally in combination with an additional acid.

In some embodiments mixtures of two or more quaternising agents may be used.

To form the quaternary ammonium salt the quaternising agent is reacted with a compound including a tertiary amine group.

Any suitable compound including a tertiary amine group may be used.

The compound including a tertiary amine group may be selected from:
(i) the reaction product of a hydrocarbyl-substituted acylating agent and a compound comprising at least one tertiary amine group and a primary amine, secondary amine or alcohol group;
(ii) a Mannich reaction product comprising a tertiary amine group;
(iii) a polyalkylene substituted amine having at least one tertiary amine group; and
(iv) an alkylamine (such as a tertiary alkylamine), an alkyl alkanolamine (such as dimethylethanolamine) and an alkanolamine.

Examples of quaternary ammonium salts and methods for preparing the same are described in the following patents: US2008/0307698, US2008/0052985, US200810113890 and US2013/031827.

The preparation of some suitable quaternary ammonium salts in which the compound including a tertiary amine group includes component (i) is described in WO 2006/135881, US2020/0024536 and WO2011/095819.

Component (ii) is a Mannich reaction product having a tertiary amine. The preparation of quaternary ammonium salts in which the compound including at least one tertiary amine group includes component (ii) is described in US 2008/0052985.

The preparation of quaternary ammonium salts in which the compound including at least one tertiary amine group includes component (iii) is described for example in US 2008/0113890.

The preparation of some suitable quaternary ammonium salts in which the compound including at least one tertiary amine group includes component (i) is described, for example in WO2016/016641.

Other suitable quaternary ammonium salts include quaternised terpolymers, for example as described in US2011/0258917; quaternised copolymers, for example as described in US2011/0315107; and the acid-free quaternised nitrogen compounds disclosed in US2012/0010112.

In some embodiments the present invention does not encompass acid-free quaternised nitrogen compounds. In preferred embodiments the quaternary ammonium salts for use in the present invention include a separate anion and a separate cation.

In some embodiments the quaternary ammonium compounds for use in the present invention are the quaternised reaction product of a fatty acid (for example oleic acid) and dimethylaminopropyl amine.

Further suitable quaternary ammonium compounds for use in the present invention include the quaternary ammonium compounds described in the applicants copending applications WO2011/095819, WO2013/017889, WO2015/011506, WO2015/011507, WO2016/016641 and WO2017/017454.

Preferably nitrogen-containing detergent (a) comprises a quaternary ammonium salt which is the quaternised reaction product of a hydrocarbyl substituted succinic acid derived acylating agent and a compound able to react with said acylating agent and which includes a tertiary amine group.

Preferably, the hydrocarbyl substituted acylated agent is a hydrocarbyl substituted succinic acid derived acylating agent.

For the avoidance of doubt, reference to the quaternised reaction product is meant to refer to a reaction product, which comprises the tertiary amine, which has then been quaternised to form a quaternary ammonium group. The quaternary ammonium salt is formed by reacting a quaternising agent with the reaction product of a hydrocarbyl-substituted succinic acid derived acylating agent and a compound able to react with said acylating agent and which includes a tertiary amine group.

As used herein, the term "hydrocarbyl substituent" or "hydrocarbyl group" is used in its ordinary sense, which is well known to those skilled in the art. Specifically, it refers to a group having a carbon atom directly attached to the remainder of the molecule and having predominantly hydrocarbon character. Examples of hydrocarbyl groups include:
  (i) hydrocarbon groups, that is, aliphatic (which may be saturated or unsaturated, linear or branched, e.g., alkyl or alkenyl), alicyclic (e.g., cycloalkyl, cycloalkenyl) substituents, and aromatic (including aliphatic- and alicyclic-substituted aromatic) substituents, as well as cyclic substituents wherein the ring is completed through another portion of the molecule (e.g., two substituents together form a ring);
  (ii) substituted hydrocarbon groups, that is, substituents containing non-hydrocarbon groups which, in the context of this invention, do not alter the predominantly hydrocarbon nature of the substituent (e.g., halo (e.g. chloro, fluoro or bromo), hydroxy, alkoxy (e.g. $C_1$ to $C_4$ alkoxy), keto, acyl, cyano, mercapto, amino, amido, nitro, nitroso, sulfoxy, nitryl and carboxy);
  (iii) hetero substituents, that is, substituents which, while having a predominantly hydrocarbon character, in the context of this invention, contain other than carbon in a ring or chain otherwise composed of carbon atoms. Heteroatoms include sulphur, oxygen, nitrogen, and encompass substituents as pyridyl, furyl, thienyl and imidazolyl. In general, no more than two, preferably no more than one, non-hydrocarbon substituent will be present for every ten-carbon atoms in the hydrocarbyl group; typically, there will be no non-hydrocarbon substituents in the hydrocarbyl group.

Suitable hydrocarbyl substituted succinic acid derived acylating agents and means of preparing them are well known in the art. For example, a common method of preparing a hydrocarbyl substituted succinic acylating agent is by the reaction of maleic anhydride with an olefin using a chlorination route or a thermal route (the so-called "ene" reaction).

Illustrative of hydrocarbyl substituent based groups include n-octyl, n-decyl, n-dodecyl, tetrapropenyl, n-octadecyl, oleyl, chloroctadecyl, triicontanyl, etc. The hydrocarbyl based substituents may be made from homo- or interpolymers (e.g. copolymers, terpolymers) of mono- and di-olefins having 2 to 10 carbon atoms, for example ethylene, propylene, butane-1, isobutene, butadiene, isoprene, 1-hexene, 1-octene, etc. Preferably, these olefins are 1-monoolefins. Alternatively the substituent may be made from other sources, for example monomeric high molecular weight alkenes (e.g. 1-tetra-contene), aliphatic petroleum fractions, for example paraffin waxes and cracked analogs thereof, white oils, synthetic alkenes for example produced by the Ziegler-Natta process (e.g. poly(ethylene) greases) and other sources known to those skilled in the art. Any unsaturation in the substituent may if desired be reduced or eliminated by hydrogenation according to procedures known in the art.

Preferably the hydrocarbyl substituents are predominantly saturated, that is, they contain no more than one carbon-to-carbon unsaturated bond for every ten carbon-to-carbon single bonds present. Most preferably they contain no more than one carbon-to-carbon non-aromatic unsaturated bond for every 50 carbon-to-carbon bonds present.

The hydrocarbyl substituent of the succinic acid derived acylating agent preferably comprises at least 10, more preferably at least 12, for example at least 30 or at least 40 carbon atoms. It may comprise up to about 200 carbon atoms. Preferably, the hydrocarbyl substituent of the acylating agent has a number average molecular weight (Mn) of between 170 to 2800, for example from 250 to 1500, preferably from 500 to 1500 and more preferably 500 to 1100. An Mn of 700 to 1300 is especially preferred.

The hydrocarbyl substituted succinic acid derived acylating agent may comprise a mixture of compounds. For example a mixture of compounds having different hydrocarbyl substituents may be used.

Preferred hydrocarbyl-based substituents are polyisobutenes. Such compounds are known to the person skilled in the art.

Preferred hydrocarbyl substituted succinic acid derived acylating agents are polyisobutenyl succinic anhydrides. These compounds are commonly referred to as "PIBSAs" and are known to the person skilled in the art.

Conventional polyisobutenes and so-called "highly-reactive" polyisobutenes are suitable for use in the invention. Highly reactive polyisobutenes in this context are defined as polyisobutenes wherein at least 50%, preferably 70% or more, of the terminal olefinic double bonds are of the vinylidene type as described in EP0565285. Particularly preferred polyisobutenes are those having more than 80 mol % and up to 100 mol % of terminal vinylidene groups such as those described in U.S. Pat. No. 7,291,758. Preferred polyisobutenes have preferred molecular weight ranges as described above for hydrocarbyl substituents generally.

Other preferred hydrocarbyl groups include those having an internal olefin for example as described in the applicant's published application WO20071015080.

An internal olefin as used herein means any olefin containing predominantly a non-alpha double bond, that is a beta or higher olefin. Preferably such materials are substantially completely beta or higher olefins, for example containing less than 10% by weight alpha olefin, more preferably less than 5% by weight or less than 2% by weight. Typical internal olefins include Neodene 151810 available from Shell.

Internal olefins are sometimes known as isomerized olefins and can be prepared from alpha olefins by a process of isomerisation known in the art, or are available from other sources. The fact that they are also known as internal olefins reflects that they do not necessarily have to be prepared by isomerisation.

Preferred hydrocarbyl substituted succinic acid derived acylating agents for use in preparing the quaternary ammonium salt (a) for use in the present invention are polyisobutenyl substituted succinic anhydrides or PIBSAs. Especially preferred PIBSAs are those having a PIB molecular weight (Mn) of from 300 to 2800, preferably from 450 to 2300, more preferably from 500 to 1300.

The hydrocarbyl substituted succinic acid derived acylating agent is suitably prepared by reacting maleic anhydride with an alkene, for example a polyisobutene. The product obtained (such as a PIBSA) still includes a double bond. The maleic anhydride is present in the resultant molecule as a succinic acid moiety. This initial product is a monomaleated PIBSA.

The monomaleated PIBSA may have the structure (A) or (B):

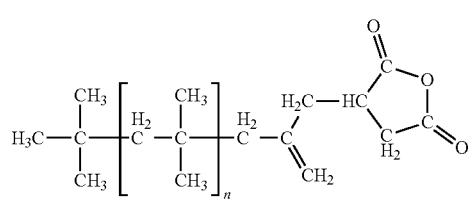

(A)

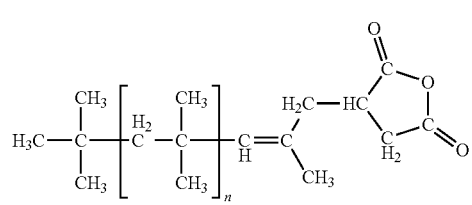

(B)

The double bond in the monomaleated product can react with a further molecule of maleic anhydride to form a bismaleated PIBSA having the structure (C) or (D):

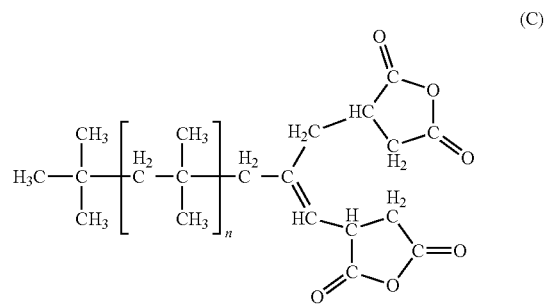

(C)

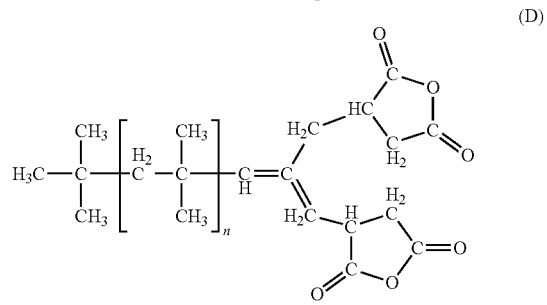

(D)

Thus it is possible to provide a hydrocarbyl group which is substituted with more than one succinic acid moiety.

The skilled person will appreciate that the hydrocarbyl substituted succinic acid derived acylating agents used in the invention typically comprise mixtures of compounds, for example mixtures of monomaleated and bismaleated PIBSAs. The PIBSAs may be defined in terms of their level of bismaleation.

One way in which this may be determined is by calculating the average number of succinic acid moieties per molecule of acylating agent.

A monomaleated PIBSA has one succinic acid moiety per module, A bismaleated PIBSA has two succinic acid moieties per molecule.

A mixture comprising monomaleated PIBSA and bismaleated PIBSA in a 1:1 molar ratio would comprise an average of 1.5 succinic acid moieties per molecule of PIBSA.

The average number of succinic acid moieties per molecule of acylating agent is sometimes referred to in the art as "P value".

Suitably the quaternary ammonium salt is prepared from a hydrocarbyl substituted succinic acid derived acylating agent comprising on average from 1 to 2 succinic acid moieties per molecule.

In some preferred embodiments the present invention may involve the use of quaternary ammonium salts derived from hydrocarbyl substituted acylating agents which include an average of at least 1.2 succinic acid moieties per molecule.

As the skilled person will appreciate, a single molecule cannot have 1.2 succinic acid moieties. What is meant by at least 1.2 succinic acid moieties is the mean number of succinic acid moieties per molecule of acylating agent as the sum of all the succinic acid moieties present in a sample divided by the total number of molecules of acylating agent having one or more succinic acid moieties present in the sample.

Preferably the hydrocarbyl substituted succinic acid derived acylating agent comprises on average at least 1.21 succinic acid moieties per molecule, more preferably at least 1.22 succinic acid moieties per molecule.

In some embodiments the hydrocarbyl substituted succinic acid derived acylating agent may comprise at least 1.23 or at least 1.24 succinic acid moieties per molecule.

In some embodiments the hydrocarbyl substituted succinic acid derived acylating agent may comprise at least 1.25, at least 1.26 or at least 1.27 succinic acid moieties per molecule.

In some embodiments the hydrocarbyl substituted succinic acid derived acylating agent may comprise at least 1.28, at least 1.29 or at least 1.30 succinic acid moieties per molecule.

By succinic acid moiety we mean to include residues of succinic acid present in diacid or anhydride form.

The hydrocarbyl substituted succinic acid derived acylating agent is reacted with a compound able to react with said acylating agent and which includes a tertiary amine group. The tertiary amine group is quaternised to provide the quaternary ammonium salt.

Examples of suitable compounds able to react with the hydrocarbyl substituted succinic acid derived acylating agent and which include a tertiary amine group can include but are not limited to: N,N-dimethylaminopropylamine, N,N-diethylaminopropylamine, N,N-dimethylamino ethylamine. The nitrogen or oxygen containing compounds capable of condensing with the acylating agent and further having a tertiary amino group can further include amino alkyl substituted heterocyclic compounds such as 1-(3 aminopropyl)imidazole and 4-(3-aminopropyl)morpholine, 1-(2-aminoethyl)piperidine, 3,3-diamino-N-methyldipropylamine, and 3'3-aminobis(N,N-dimethylpropylamine). Other types of nitrogen or oxygen containing compounds capable of condensing with the acylating agent and having a tertiary amino group include alkanolamines including but not limited to triethanolamine, trimethanolamine, N,N-dimethylaminopropanol, N,N-dimethylaminoethanol, N,N-diethylaminopropanol, N,N-diethylaminoethanol, N,N-diethylaminobutanol, N,N,N-tris(hydroxyethyl)amine, N,N,N-tris(hydroxymethyl)amine, N,N,N-tris(aminoethyl)amine, N,N-dibutylaminopropylamine and N,N,N'-trimethyl-N'-hydroxyethyl-bisaminoethylether; N,N-bis(3-dimethylaminopropyl)-N-isopropanolamine; N-(3-dimethylaminopropyl)-N,N-diisopropanolamine; N'-(3-(dimethylamino)propyl)-N,N-dimethyl 1,3-propanediamine; 2-(2-dimethylaminoethoxy)ethanol, N,N,N'-trimethylaminoethylethanolamine and 3-(2-(dimethylamino)ethoxy) propylamine.

Preferably the compound able to react with hydrocarbyl substituted succinic acid derived acylating agent and which includes a tertiary amine group is an amine of formula (II) or (III):

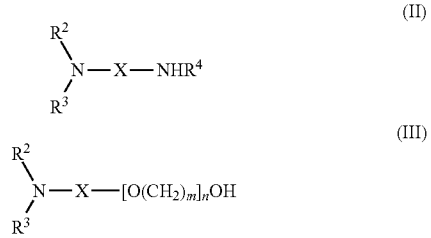

wherein $R^2$ and $R^3$ are the same or different alkyl, alkenyl, aryl, alkaryl or aralkyl groups having from 1 to 22 carbon atoms; X is a bond or an optionally substituted alkylene group having from 1 to 20 carbon atoms; n is from 0 to 20; m is from 1 to 5; and $R^4$ is hydrogen or a $C_1$ to $C_{22}$ alkyl group.

When a compound of formula (II) is used, $R^4$ is preferably hydrogen or a $C_1$ to $C_{16}$ alkyl group, preferably a $C_1$ to $C_{10}$ alkyl group, more preferably a $C_1$ to $C_6$ alkyl group. When $R^4$ is alkyl it may be straight chained or branched. It may be substituted for example with a hydroxy or alkoxy substituent. Preferably $R^4$ is not a substituted alkyl group. More preferably $R^4$ is selected from hydrogen, methyl, ethyl, propyl, butyl and isomers thereof. Most preferably $R^4$ is hydrogen.

When a compound of formula (III) is used, m is preferably 2 or 3, most preferably 2; n is preferably from 0 to 15, preferably 0 to 10, more preferably from 0 to 5. Most preferably n is 0 and the compound of formula (III) is an alcohol.

Preferably the hydrocarbyl substituted acylating agent is reacted with a diamine compound of formula (II).

$R^2$ and $R^3$ are the same or different alkyl, alkenyl, aryl, alkaryl or aralkyl groups having from 1 to 22 carbon atoms. In some embodiments $R^2$ and $R^3$ may be joined together to form a ring structure, for example a piperidine, imidazole or morpholine moiety. Thus $R^2$ and $R^3$ may together form an aromatic and/or heterocyclic moiety. $R^2$ and $R^3$ may be branched alkyl or alkenyl groups. Each may be substituted, for example with a hydroxy or alkoxy substituent.

Preferably each of $R^2$ and $R^3$ is independently a $C_1$ to $C_{15}$ alkyl group, preferably a $C_1$ to $C_{10}$ alkyl group. $R^2$ and $R^3$ may independently be methyl, ethyl, propyl, butyl, pentyl, hexyl, heptyl, octyl, or an isomer of any of these. Preferably $R^2$ and $R^3$ is each independently $C_1$ to $C_4$ alkyl. Preferably $R^2$ is methyl. Preferably $R^3$ is methyl.

X is a bond or an optionally substituted alkylene group having from 1 to 20 carbon atoms. In preferred embodiments when X is an alkylene group this group may be straight chained or branched. The alkylene group may include a cyclic structure therein. It may be optionally substituted, for example with a hydroxy or alkoxy substituent. In some embodiments X may include a heteroatom within the alkylene chain, for example X may include an ether functionality.

X is preferably an alkylene group having 1 to 16 carbon atoms, preferably 1 to 12 carbon atoms, more preferably 1 to 8 carbon atoms, for example 2 to 6 carbon atoms or 2 to 5 carbon atoms. In some preferred embodiments X is an unsubstituted alkylene group. Most preferably X is an ethylene, propylene or butylene group, especially a propylene group.

Examples of compounds of formula (II) suitable for use herein include 1-aminopiperidine, 1-(2-aminoethyl)piperidine, 1-(3-aminopropyl)-2-pipecoline, 1-methyl-(4-methylamino)piperidine, 4-(1-pyrrolidinyl)piperidine, 1-(2-aminoethyl)pyrrolidine, 2-(2-aminoethyl)-1-methylpyrrolidine, N,N-diethylethylenediamine, N,N-dimethylethylenediamine, N,N-dibutylethylenediamine, N,N-diethyl-1,3-diaminopropane, N,N-dimethyl-1,3-diaminopropane, N,N,N-trimethylethylenediamine, N,N-dimethyl-N-ethylethylenediamine, N,N-diethyl-N'-methylethylenediamine, N,N,N'-triethylethylenediamine, 3-dimethylaminopropylamine, 3-diethylaminopropylamine, 3-dibutylaminopropylamine, N,N,N' trimethyl-1,3-propanediamine, N,N,2,2-tetramethyl-1,3-propanediamine, 2-amino-5-diethylaminopentane, N,N,N',N'-tetraethyldiethylenetriamine, 3,3'-diamino-N-methyldipropylamine, 3,3'-iminobis(N,N-dimethylpropylamine), 1-(3-aminopropyl) imidazole and 4-(3-aminopropyl)morpholine, 1-(2- aminoethyl)piperidine, 3,3-diamino-N-methyldipropylamine, 3,3-aminobis(N,N-dimethylpropylamine), 3-(2-(dimethylamino)ethoxy) propylamine, or combinations thereof.

In some preferred embodiments the compound of formula (II) is selected from N,N-dimethyl-1,3-diaminopropane, N,N-diethyl-1,3-diaminopropane, N,N-dimethylethylenediamine, N,N-diethylethylenediamine, N,N-dibutylethylenediamine, 3-(2-(dimethylamino)ethoxy) propylamine, or combinations thereof.

Examples of compounds of formula (III) suitable for use herein include alkanolamines including but not limited to triethanolamine, N,N-dimethylaminopropanol, N,N-diethylaminopropanol, N,N-diethylaminobutanol, triisopropanolamine, 1-[2-hydroxyethyl]piperidine, 2-[2-(dimethylamine)ethoxy]-ethanol, N-ethyldiethanolamine, N-methyldiethanolamine, N-butyldiethanolamine, N,N-diethylaminoethanol, N,N-dimethyl amino-ethanol, 2-dimethylamino-2-methyl-1-propanol, N,N,N-trimethyl-N-hydroxyethyl-bisaminoethylether; N,N-bis(3-dimethylaminopropyl)-N-isopropanolamine; N-(3-dimethylaminopropyl)-N,N-diisopropanolamine; N'-(3-(dimethylamino)propyl)-N,N-dimethyl 1,3-propanediamine; 2-(2-dimethylaminoethoxy)ethanol, and N,N,N'-trimethylaminoethylethanolamine.

In some preferred embodiments the compound of formula (III) is selected from Triisopropanolamine, 1-[2-hydroxyethyl]piperidine, 2-[2-(dimethylamine)ethoxy]-ethanol, N-ethyldiethanolamine, N-methyldiethanolamine, N-butyldiethanolamine, N,N-diethylaminoethanol, N,N-dimethylaminoethanol, 2-dimethylamino-2-methyl-1-propanol, or combinations thereof.

An especially preferred compound of formula (II) is N,N-dimethyl-1,3-diaminopropane (dimethylaminopropylamine).

When a compound of formula (III) is reacted with a succinic acylating agent the resulting product is a succinic ester. When a succinic acylating agent is reacted with a compound of formula (II) in which $R^4$ is hydrogen the resulting product may be a succinimide or a succinamide. When a succinic acylating agent is reacted with a compound of formula (II) in which $R^4$ is not hydrogen the resulting product is an amide.

To form the quaternary ammonium salt (a) the hydrocarbyl substituted succinic acid derived acylating agent is reacted with a compound able to react with said acylating agent and which includes a tertiary amine group. This reaction product is then quaternised by reaction with a quaternising agent.

The reaction product of the acylating agent and compound which includes a tertiary amine group is preferably reacted with at least one molar equivalent of quaternising agent per mole of tertiary amine group present in the reaction product.

In some embodiments the reaction product of the acylating agent and compound which includes a tertiary amine group may be reacted with more than one molar equivalent of quaternising agent per mole of tertiary amine group present in the reaction product, preferably at least 1.2 molar equivalents of quaternising agent per mole of tertiary amine group, more preferably at least 1.5 molar equivalents of quaternising agent, suitably at least 17 molar equivalents of quaternising agent, for example at least 1.9 molar equivalents of quaternising agent.

In some embodiments the reaction product of the acylating agent and compound which includes a tertiary amine group may be reacted with two or more molar equivalents of quaternising agent per mole of tertiary amine group present in the reaction product, preferably at least 2.1 molar equivalents of quaternising agent.

In some embodiments the reaction product of the acylating agent and compound which includes a tertiary amine group is reacted with more than 2.2 molar equivalents of quaternising agent per mole of tertiary amine group present in the reaction product, for example from 2.3 to 4 molar equivalents, from 2.3 to 3 molar equivalents, or from 2.3 to 2.7 or from 2.5 to 3 molar equivalents.

To form some preferred quaternary ammonium salts for use in the present invention the compound of formula (I) is reacted with a compound formed by the reaction of a hydrocarbyl substituted acylating agent and an amine of formula (II) or (III).

The compounds of formula (II) or formula (III) are as described above.

Preferably the amine of formula (II) or (III) is reacted with a hydrocarbyl substituted succinic acid derived acylating agent such as a succinic acid or succinic anhydride.

Suitably approximately one equivalent of amine is added per succinic acid moiety present in the acylating agent. The ratio of amine used will thus typically depend on the average number of succinic acid moieties present in each molecule of the acylating agent.

Preferred quaternary ammonium salts for use herein may be formed by reacting methyl salicylate, dimethyl oxalate or propylene oxide optionally in combination with an acid with the reaction product of a polyisobutylene-substituted succinic anhydride having a PIB molecular weight of 700 to 1300 and dimethylaminopropylamine.

Preferred quaternary ammonium salts for use herein may be formed by reacting chloroacetic acid or a salt thereof with the reaction product of a oleic acid or a reactive derivative thereof and dimethylaminopropylamine.

An especially preferred quaternary ammonium salt for use herein is formed by reacting methyl salicylate or dimethyl oxalate with the reaction product of a polyisobutylene-substituted succinic anhydride having a PIB molecular weight of 700 to 1300 and dimethylaminopropylamine.

In one preferred embodiment the polyisobutylene-substituted succinic anhydride includes on average at least 1.2 succinic acid moieties per molecule.

In some embodiments the present invention involves the use as an additive of (b) the reaction product of a carboxylic acid-derived acylating agent and an amine.

These compounds may also be referred to herein in general as acylated nitrogen-containing compounds.

Suitable acylated nitrogen-containing compounds may be made by reacting a carboxylic acid acylating agent with an amine and are known to those skilled in the art.

Preferred hydrocarbyl substituted acylating agents are polyisobutenyl succinic anhydrides. These compounds are commonly referred to as "PIBSAs" and are known to the person skilled in the art.

Conventional polyisobutenes and so-called "highly-reactive" polyisobutenes are suitable for use in the invention. These are suitably as previously described herein in relation to the preparation of some preferred quaternary ammonium detergents.

Especially preferred PIBSAs are those having a PIB molecular weight (Mn) of from 300 to 2800, preferably from 450 to 2300, more preferably from 500 to 1300.

In preferred embodiments the reaction product of the carboxylic acid derived acylating agent and an amine includes at least one primary or secondary amine group.

A preferred acylated nitrogen-containing compound for use herein is prepared by reacting a poly(isobutene)-substituted succinic acid-derived acylating agent (e.g., anhydride, acid, ester, etc.) wherein the poly(isobutene) substituent has a number average molecular weight (Mn) of between 170 to 2800 with a mixture of ethylene polyamines having 2 to about 9 amino nitrogen atoms, preferably about 2 to about 8 nitrogen atoms, per ethylene polyamine and about 1 to about 8 ethylene groups. These acylated nitrogen compounds are suitably formed by the reaction of a molar ratio of acylating agent:amino compound of from 10:1 to 1:10, preferably from 5:1 to 1:5, more preferably from 2:1 to 1:2 and most preferably from 2:1 to 1:1. In especially preferred embodiments, the acylated nitrogen compounds are formed by the reaction of acylating agent to amino compound in a molar ratio of from 1.8:1 to 1:1.2, preferably from 1.6:1 to 1:1.2, more preferably from 1.4:1 to 1:1.1 and most preferably from 1.2:1 to 1:1. Acylated amino compounds of this type and their preparation are well known to those skilled in the art and are described in for example EP0565285 and U.S. Pat. No. 5,925,151.

A preferred nitrogen-containing detergent is of the type formed by the reaction of a polyisobutene-substituted succinic acid-derived acylating agent and a polyethylene polyamine. Suitable compounds are, for example, described in WO2009/040583.

In a preferred embodiment the reaction product of a carboxylic acid-derived acylating agent and an amine (b) comprises the reaction product of a polyisobutene-substituted succinic acid or succinic anhydride and a polyethylene polyamine selected from ethylenediamine, diethylenetriamine, triethylenetetramine, tetraethylenepentamine, pentaethylenehexamine, hexaethylene-heptamine and mixtures and isomers thereof; wherein polyisobutene substituent has a number average molecular weight of between 500 and 2000, preferably between 600 and 1000.

In some embodiments the present invention may involve the use of (c) the product of a Mannich reaction between an aldehyde, an amine and an optionally substituted phenol.

Preferably component (c) comprises the product of a Mannich reaction between:
(x) an aldehyde;
(y) an amine; and
(z) an optionally substituted phenol.

Preferably the aldehyde component used to prepare the Mannich reaction product is an aliphatic aldehyde. Preferably the aldehyde has 1 to 10 carbon atoms. Most preferably the aldehyde is formaldehyde.

Suitable amines for use in preparing the Mannich reaction product include monoamines and polyamines. One suitable monoamine is butylamine.

The amine used to prepare the Mannich reaction product is preferably a polyamine. This may be selected from any compound including two or more amine groups. Preferably the polyamine is a polyalkylene polyamine, preferably a polyethylene polyamine. Most preferably the polyamine comprises tetraethylenepentamine or ethylenediamine.

The optionally substituted phenol component used to prepare the Mannich additive may be substituted with 0 to 4 groups on the aromatic ring (in addition to the phenol OH). For example it may be a hydrocarbyl-substituted cresol. Most preferably the phenol component is a mono-substituted phenol. Preferably it is a hydrocarbyl substituted phenol. Preferred hydrocarbyl substituents are alkyl substituents having 4 to 28 carbon atoms, especially 10 to 14 carbon atoms. Other preferred hydrocarbyl substituents are polyalkenyl substituents. Such polyisobutenyl substituents having a number average molecular weight of from 400 to 2500, for example from 500 to 1500.

Preferred Mannich reaction products used in the present invention are typically formed by reacting components (x), (y) and (z) in a molar ratio of 1.1 to 5 parts (x) to 1 part (y) to 1.1 to 2 parts (z).

Suitable Mannich reaction products and methods of preparing such Mannich reaction products will be known to the person skilled in the art and include the compounds described, for example, in the applicant's publications WO2009040582 and WO2013017887.

Preferred Mannich reaction products are the reaction product of formaldehyde, a polyethylene polyamine; and a para-substituted monoalkyl phenol.

An especially preferred Mannich reaction product for use herein is the reaction product of dodecyl phenol, formaldehyde and ethylene diamine.

Suitable treat rates of the at least one nitrogen-containing detergent may depend on the type of fuel used and different levels of nitrogen-containing detergent may be needed to achieve different levels of performance.

The at least one nitrogen-containing detergent may be added to fuel at any convenient place in the supply chain. For example, the at least one nitrogen-containing detergent may be added to fuel at the refinery, at a distribution terminal or after the fuel has left the distribution terminal. The at least one nitrogen-containing detergent may be added to the renewable diesel component and/or the biodiesel component before the components are blended; and/or the at least one nitrogen-containing detergent may be added to the blended fuel after the components have been mixed. If the at least one nitrogen-containing detergent is added to the fuel after it has left the distribution terminal, this is termed an aftermarket application. Aftermarket applications include such circumstances as adding the at least one nitrogen-containing detergent to the fuel in the delivery tanker, directly to a customer's bulk storage tank, or directly to the end user's vehicle tank. Aftermarket applications may include supplying the at least one nitrogen-containing detergent in small bottles suitable for direct addition to fuel storage tanks or vehicle tanks.

The at least one nitrogen-containing detergent is suitably present in the fuel composition in an amount of at least 1 ppm, preferably at least 2 ppm, suitably at least 5 ppm.

The at least one nitrogen-containing detergent may be present in the fuel composition in an amount of up to 1000 ppm, suitably up to 750 ppm, for example up to 600 ppm.

The at least one nitrogen-containing detergent is preferably present in the fuel composition an amount of from the 1 to 1000 ppm, preferably 2 to 500 ppm, for example 5 to 350 ppm.

For the avoidance of doubt when the fuel composition comprises a mixture of two or more nitrogen-containing detergents, the above amounts refer to the total amount of all nitrogen-containing detergents present in the composition. Unless otherwise stated, all references to ppm in this specification are to parts per million by weight.

In preferred embodiments the fuel composition comprises one or more of:
(a) a quaternary ammonium salt;
(b) the reaction product of a carboxylic acid-derived acylating agent and an amine; and
(c) the product of a Mannich reaction between an aldehyde, an amine and an optionally substituted phenol.

In some embodiments the fuel composition comprises from 0.1 to 10000 ppm, preferably from 1 to 1000 ppm, preferably from 5 to 500 ppm, for example 10 to 250 ppm of (a) a quaternary ammonium salt.

In some embodiments the fuel composition comprises from 0.1 to 10000 ppm, preferably from 1 to 1000 ppm, preferably from 5 to 500 ppm, for example 10 to 250 ppm of (b) the reaction product of a carboxylic acid-derived acylating agent and an amine.

In some embodiments the fuel composition comprises from 0.1 to 10000 ppm, preferably from 1 to 1000 ppm, preferably from 5 to 500 ppm, for example 10 to 250 ppm of (c) the product of a Mannich reaction between an aldehyde, an amine and an optionally substituted phenol.

Each of the nitrogen-containing detergents (a), (b) and (c) may be provided as a mixture of compounds. Each of the nitrogen-containing detergents (a), (b) and (c) may be provided as a crude reaction product, i.e. without purification after preparation. The above amounts refer to the total of all such compounds present in the composition.

For the avoidance of doubt the above amounts refer to the amount of active nitrogen-containing detergent compound present in the composition and ignore any impurities, solvents or diluents which may be present.

In some preferred embodiments the fuel composition comprises (a) a quaternary ammonium salt and (c) the product of a Mannich reaction between an aldehyde, an amine and an optionally substituted phenol.

Preferably the fuel composition comprises from 5 to 500 ppm, preferably 10 to 250 ppm of (a) a quaternary ammonium salt and from 5 to 500 ppm, preferably 10 to 250 ppm of (c) the product of a Mannich reaction between an aldehyde, an amine and an optionally substituted phenol.

In some embodiments the fuel composition comprises (a) a quaternary ammonium salt and (c) the product of a Mannich reaction between an aldehyde, an amine and an optionally substituted phenol, suitably in a weight ratio of from 3:1 to 1:3, preferably around 1:1; wherein component (a) comprises a quaternary ammonium salt formed by reacting methyl salicylate, dimethyl oxalate or propylene oxide (optionally in combination with an acid) with the reaction product of a polyisobutylene-substituted succinic anhydride having a PIB molecular weight of 700 to 1300 and dimethylaminopropylamine; and component (c) comprises the reaction product of formaldehyde, a polyethylene polyamine and a para-substituted monoalkyl phenol, preferably dodecyl phenol.

The fuel composition of the present invention may include one or more further additives such as those which are commonly found in diesel fuels. These include, for example, antioxidants, dispersants, detergents, metal deactivating compounds, wax anti-settling agents, cold flow improvers, cetane improvers, dehazers, stabilisers, demulsifiers, antifoams, corrosion inhibitors, lubricity improvers, dyes, markers, combustion improvers, metal deactivators, odour masks, drag reducers and conductivity improvers. Examples of suitable amounts of each of these types of additives will be known to the person skilled in the art.

The present invention relates to reducing the filter blocking tendency of a fuel composition having a tendency to block filters.

By a fuel composition having a tendency to block filters we mean to refer to a fuel composition which, if untreated with at least one nitrogen-containing detergent as described herein, would cause blocking of filters. The tendency of a fuel composition to block filters may be measured by a number of standard industry tests. The fuel compositions suitable for treatment according to the present invention are fuel compositions which do not satisfy the requirements of such standard tests without the addition of the claimed at least one nitrogen-containing detergent.

Reduction of the filter blocking tendency of the fuel compositions may be demonstrated by achieving an improved performance in one of these tests.

Standard test methods for determining filter blocking tendency (FBT) are described in ASTM D2068 and IP387. This general procedure is commonly used for middle distillate fuels containing biodiesel and biodiesel blends. Another test suitable for measuring filter blocking tendency is set out in IP618. The present invention may be assessed using one of these tests.

A preferred method by which the filter blocking tendency of the present invention can be determined is the Canadian Cold Soak Filter Blocking Tendency test (CSFBT). In this test fuel is stored at 1° C. for 16 hours before the filterability is assessed. The procedure for this test is set out in CAN/CGSB 3.0 No. 142.0-2019 and a modified version in which renewable fuel is used in place of a specified isoparaffinic solvent is described in example 2. A similar test is the European Cold Soak test CS IP387 in which fuel is stored at 5° C. for 16 hours.

In preferred embodiments the present invention reduces the filter blocking tendency of the fuel composition as measured by the method of the CSFBT test. According to the method the CSFBT test fuel compositions are cooled to 1° C. for 16 hours and then tested by filtration to provide a unitless value. The value is an indicator of how likely the fuel is to block filters and a value of less than 2 is generally considered acceptable.

Preferably the present invention reduces the filter blocking tendency of a fuel composition which achieves a CSFBT test result of greater than 2 prior to being treated with at least one nitrogen-containing detergent according to the invention. Suitably a fuel composition provided by the present invention achieves a CSFBT test result of less than 2.

Preferably the present invention reduces the score of a fuel composition in a CSFBT test by at least 10%, suitably at least 20%, more preferably at least 30%, for example at least 40% or at least 50%.

The invention will now be further described with further to the following non-limiting examples.

Example 1

Additive A, a nitrogen-containing detergent which is a Mannich reaction product, was prepared as follows:

To a 1L jacketed glass reactor, was transferred 4-dodecylphenol (129.6 g, 0.494 moles, 1.7 equivalents). Aromatic A150 solvent (95.2 g) was added and heated to 75° C. Ethylenediamine (17.5 g, 0.291 moles, 1 equiv) was added and the mixture was heated to 90° C. 37% aq formalin (94.3 g, 1.16 moles, 4 equivs) was then added, keeping the reaction mixture temperature in the range 90-96° C. The reactor was sealed, and the temperature increased to 120° C. over 3 hours. This was accompanied by a pressure increase to 0.8 barg. The reaction mixture was held for 3 hours at 120-122° C., at pressure up to 1.1 barg. The reaction temperature was then decreased to ~95° C. and the pressure dropped to <0.5 bar, at which point the reactor was opened to the atmosphere. Agitation was stopped and the contents allowed to separate. The amber organic phase was washed twice with water at 90-90° C. Finally, any residual water was removed from the organic phase under reduced pressure, leaving a clear and bright amber liquid (235 g).

Example 2

Additive B, a nitrogen-containing detergent which is a quaternary ammonium salt, was prepared as follows:

HR 1000 MW polyisobuylene (126.37 g, 126 mmol, 1.0 eqs) was heated to 190° C. then maleic anhydride (12.47 g, 127 mmol, 1.0 eqs) was added over 1 hour. The reaction was heated to 205° C. then held for eight hours. Unreacted maleic anhydride was removed by vacuum distillation. The resulting PIBSA was cooled to 120° C. and DMAPA (11.9 g, 116 mmol, 0.9 eq) charged keeping the reaction temperature in the range 120° C.-130° C. The reaction mixture was stirred then the temperature was increased to 140° C. to allow distillation of water. Once distillation was complete methyl salicylate (17.36 g, 114 mmol, 0.9 equivs) was charged and the reaction heated at 140° C. until the reaction was complete. The reaction mixture was diluted with solvent then cooled and discharged (271.2 g).

Example 3

A commercially sourced fuel composition comprising a blend of 80% by volume of a renewable diesel and 20% by volume of a biodiesel was treated with 1000 ppm of an additive composition (additive composition G below) comprising an aromatic solvent, 15 wt % additive A and 14 wt % additive B.

The untreated blended fuel had the following properties:

| Cloud Point, ASTM D7689 (° C.) | CFPP, ASTM D6371 (° C.) | Pour Point, ASTM D7346 (° C.) |
|---|---|---|
| 2.4 | 0 | 0 |

Example 4

The unadditised and additised fuel compositions described in example 3 were tested according to a modification of the procedure of the standard CSFBT test method set out in CAN/CGSB 3.0, No. 142-2019.

The summary of the modified test method is as follows:
1. A sample of the fuel composition is first conditioned to erase its thermal history.
2. The fuel composition is then held at 1° C. for 16 h.
3. The fuel composition is then warmed to 25° C. for 2-4 h.
4. After warming, the fuel composition is then passed at a constant rate of flow (20 mL/min) through a glass fibre filter medium (1.6 μm pore size).
4.1. The pressure drop across the filter is monitored until 300 mL of the fuel composition has passed through the filter, and the maximum pressure drop is used to calculate the CSFBT result, or
4.2. If a pressure drop of 105 kPa is reached before 300 mL of the fuel composition is filtered, the volume filtered when 105 kPa is reached is used to calculate the CSFBT result.
5. Results of the CSFBT test can range from 1.0 for a fuel composition with very good filterability (essentially no separated materials under the test conditions), to more than 10 for a fuel composition with poor filterability (a relatively high level of separated materials under test conditions).

The results are shown in Table 1.

TABLE 1

| Fuel | FBT |
|---|---|
| Base fuel | 3.88 |
| Additised fuel | 1.56 |

A blended fuel composition was prepared comprising 80% by volume of a renewable diesel fuel (R100) and 20% by volume of a biodiesel fuel (B100).

The unblended fuel components had the following properties:

| Fuel | Cloud Point (° C.) (ASTM D7689) | Pour Point (° C.) (ASTM D7346) |
|---|---|---|
| R100 | −11.4 | −12.2 |
| B100 | −2 | −3 |

Fuel compositions were prepared by dosing the following additives into the blended fuel composition:

Additive C comprises a Mannich reaction product prepared from the reaction of dodecylphenol, ethylenediamine and formaldehyde, using a method analogous to that described in comparative example 2 of WO2013017886A1. After completion of the reaction, the active material content of Additive C was adjusted to 29 wt % by dilution with Aromatic 150 solvent.

Additive D is a solution (in aromatic solvent) of a polyisobutenyl succinimide obtained from the condensation reaction of a polyisobutenyl succinic anhydride derived from polyisobutene of Mn approximately 750 with a polyethylene polyamine mixture of average composition approximating to tetraethylene pentamine. The product was obtained by mixing the polyisobutenyl succinic anhydride and tetraethylene pentamine at 50° C. under nitrogen and heating at 160° C. for 5 hours with removal of water. After completion of the reaction, the active material content of Additive D was adjusted to 29 wt % by dilution with Aromatic 150 solvent.

Additive E was prepared by the quaternization of a succinamide with propylene oxide in the absence of an additional acid, using a procedure analogous to that described in preparation example 1 of U.S. Pat. No. 9,255,236B2. Propylene oxide was used for the quaternization reaction, instead of styrene oxide. The succinamide precursor was prepared by the reaction of polyisobutylene succinic anhydride (PIBSA) having a PIB number average molecular weight of 1000 with dimethylaminopropylamine (DMAPA), at 20-25° C. After completion of the reaction, the active material content of Additive E was adjusted to 29 wt % by dilution with Aromatic 150 solvent.

Additive F was prepared according to the following procedure:

Oleylamidopropyl dimethylamine (183.5 g, 0.5 mol), isopropanol (68 mL), water (25.5 mL) and sodium chloroacetate (56.5 g, 0.48 mol) were charged to a 1 L reactor and heated to 80° C. for 6 hours with stirring. After cooling to 60° C., isopropanol (300 mL) and 2-ethylhexanol (67.5 g) were added and the reaction temperature increased to 90° C. Volatile liquids were distilled off over a 2 hour period. Residual isopropanol and water were then removed by applying vacuum (about 50 mbar) whilst maintaining heating. The reaction mass was cooled to about 75° C. then filtered through a glass microfibre filter under vacuum. The filtrate was then diluted with Aromatic 150 solvent to provide Additive F, a 29 wt % solution of the quaternized reaction product.

Additive composition G comprised an aromatic solvent, 15 wt % additive A and 14 wt % additive B.

The additives were dosed into the blended fuel and tested according to a modification of the procedure of the standard CSFBT test method set out in CAN/CGSB 3.0, No. 142-2019 and described in example 4.

The results are shown in Table 2.

TABLE 2

| Additive | Treat rate (ppm additive by weight) | FBT |
|---|---|---|
| None | 0 | 3.48 |
| G | 1000 | 1.11 |
| C | 1000 | 1.74 |
| B | 1000 | 1.02 |
| D | 1000 | 1.02 |
| F | 1000 | 1.00 |
| E | 1000 | 1.02 |

The invention claimed is:

1. A method of reducing the filter blocking tendency of a fuel composition having a tendency to block filters and which comprises 1 to 40 vol % of a biodiesel component and from 60 to 99 vol % of a renewable diesel component, the method comprising dosing into the fuel at least one nitrogen-containing detergent.

2. A fuel composition comprising from 60 to 99 vol % of a renewable diesel component, 1 to 40 vol % of a biodiesel component and least one nitrogen-containing detergent; wherein the fuel composition has a reduced filter blocking tendency compared with an otherwise identical fuel composition which does not comprise the nitrogen-containing detergent and has a tendency to block filters.

3. The composition according to claim 2, wherein the at least one nitrogen-containing detergent is selected from one or more of:
  (a) a quaternary ammonium salt;
  (b) the reaction product of a carboxylic acid-derived acylating agent and an amine;
  (c) the product of a Mannich reaction between an aldehyde, an amine and an optionally substituted phenol;
  (d) the reaction product of a carboxylic acid-derived acylating agent and hydrazine;
  (e) a salt formed by the reaction of a carboxylic acid with di-n-butylamine or tri-n-butylamine; and
  (f) the reaction product of a hydrocarbyl-substituted dicarboxylic acid or anhydride and an amine compound or salt which product comprises at least one amino triazole group.

4. The composition according to claim 3 wherein the at least one nitrogen-containing detergent comprises a quaternary ammonium salt.

5. The composition according to claim 4 wherein the quaternary ammonium salt is the reaction product of a compound including at least one tertiary amine group and a quaternising agent.

6. The composition according to claim 5 wherein the quaternising agent is selected from esters of a carboxylic acid, dialkyl sulfates, benzyl halides, hydrocarbyl substituted carbonates, hydrocarbyl substituted epoxides optionally in combination with an acid, alkyl halides, alkyl sulfonates, sultones, hydrocarbyl substituted phosphates, hydrocarbyl substituted borates, alkyl nitrites, alkyl nitrates, hydroxides, N-oxides, chloroacetic acid or salts thereof, or mixtures thereof.

7. The composition according to claim 4 wherein the compound including at least one tertiary amine group is selected from:
  (i) the reaction product of a hydrocarbyl-substituted acylating agent and a compound comprising at least one tertiary amine group and a primary amine, secondary amine or alcohol group;
  (ii) a Mannich reaction product comprising a tertiary amine group;
  (iii) a polyalkylene substituted amine having at least one tertiary amine group; and
  (iv) an alkylamine, an alkyl alkanolamine and an alkanolamine.

8. The composition according to claim 4 wherein the quaternary ammonium salt is the quaternised reaction product of a hydrocarbyl substituted succinic acid derived acylating agent and a compound able to react with said acylating agent and which includes a tertiary amine group.

9. The composition according to claim 4 wherein the quaternary ammonium salt is formed by reacting methyl salicylate, dimethyl oxalate or propylene oxide optionally in combination with an acid with the reaction product of a polyisobutylene-substituted succinic anhydride having a PIB molecular weight of 700 to 1300 and dimethylaminopropylamine.

10. The composition according to claim 4 wherein the quaternary ammonium salt is formed by reacting chloroacetic acid or a salt thereof with the reaction product of oleic acid or a reactive derivative thereof and dimethylaminopropylamine.

11. The composition according to claim 3 wherein the at least one nitrogen-containing detergent comprises the product of a Mannich reaction between an aldehyde, an amine and an optionally substituted phenol.

12. The composition according to claim 2 which provides an improved filter blocking tendency as measured by the Canadian Cold Soak Filter Blocking Tendency test CAN/CGSB-3.0 No. 142.0-2019.

13. The method according to claim 1, wherein the at least one nitrogen-containing detergent is selected from one or more of:
  (a) a quaternary ammonium salt;
  (b) the reaction product of a carboxylic acid-derived acylating agent and an amine;
  (c) the product of a Mannich reaction between an aldehyde, an amine and an optionally substituted phenol;
  (d) the reaction product of a carboxylic acid-derived acylating agent and hydrazine;
  (e) a salt formed by the reaction of a carboxylic acid with di-n-butylamine or tri-n-butylamine; and
  (f) the reaction product of a hydrocarbyl-substituted dicarboxylic acid or anhydride and an amine compound or salt which product comprises at least one amino triazole group.

14. The method according to claim 1 wherein the at least one nitrogen-containing detergent comprises a quaternary ammonium salt.

15. The method according to claim 14 wherein the quaternary ammonium salt is the reaction product of a compound including at least one tertiary amine group and a quaternising agent.

16. The method according to claim 15 wherein the quaternising agent is selected from esters of a carboxylic acid, dialkyl sulfates, benzyl halides, hydrocarbyl substituted carbonates, hydrocarbyl substituted epoxides optionally in combination with an acid, alkyl halides, alkyl sulfonates, sultones, hydrocarbyl substituted phosphates, hydrocarbyl substituted borates, alkyl nitrites, alkyl nitrates, hydroxides, N-oxides, chloroacetic acid or salts thereof, or mixtures thereof.

17. The method according to claim 14 wherein the compound including at least one tertiary amine group is selected from:
   (i) the reaction product of a hydrocarbyl-substituted acylating agent and a compound comprising at least one tertiary amine group and a primary amine, secondary amine or alcohol group;
   (ii) a Mannich reaction product comprising a tertiary amine group;
   (iii) a polyalkylene substituted amine having at least one tertiary amine group; and
   (iv) an alkylamine, an alkyl alkanolamine and an alkanolamine.

18. The method according to claim 14, wherein the quaternary ammonium salt is the quaternised reaction product of a hydrocarbyl substituted succinic acid derived acylating agent and a compound able to react with said acylating agent and which includes a tertiary amine group.

19. The method according to claim 14, wherein the quaternary ammonium salt is formed by reacting methyl salicylate, dimethyl oxalate or propylene oxide optionally in combination with an acid with the reaction product of a polyisobutylene-substituted succinic anhydride having a PIB molecular weight of 700 to 1300 and dimethylaminopropylamine.

20. The method according to claim 14, wherein the quaternary ammonium salt is formed by reacting chloroacetic acid or a salt thereof with the reaction product of oleic acid or a reactive derivative thereof and dimethylaminopropylamine.

21. The method according to claim 13, wherein the at least one nitrogen-containing detergent comprises the product of a Mannich reaction between an aldehyde, an amine and an optionally substituted phenol.

22. The method according to claim 1, which provides an improved filter blocking tendency as measured by the Canadian Cold Soak Filter Blocking Tendency test CAN/CGSB-3.0 No. 142.0-2019.

* * * * *